(12) United States Patent
Brinker

(10) Patent No.: US 8,240,471 B2
(45) Date of Patent: Aug. 14, 2012

(54) FOLDABLE STERILE MEDICAL PACKAGE

(75) Inventor: Benjamin Brinker, Plainville, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 13/105,355

(22) Filed: May 11, 2011

(65) Prior Publication Data

US 2011/0253573 A1    Oct. 20, 2011

Related U.S. Application Data

(63) Continuation of application No. 12/569,047, filed on Sep. 29, 2009, now Pat. No. 7,967,139.

(60) Provisional application No. 61/100,796, filed on Sep. 29, 2008.

(51) Int. Cl.
*A61B 19/02* (2006.01)

(52) U.S. Cl. .................... 206/438; 206/472; 206/570

(58) Field of Classification Search .................. 206/205, 206/210, 363, 370, 438–441, 472–475, 570–572; 229/87.01–87.05; 422/26, 28, 34, 294
See application file for complete search history.

(56) References Cited

U.S. PATENT DOCUMENTS

| | | | | |
|---|---|---|---|---|
| 1,356,078 A | * | 10/1920 | McGann | 206/473 |
| 2,050,270 A | * | 8/1936 | Burnham | 206/475 |
| 2,476,740 A | | 7/1949 | Krall | |
| 2,652,149 A | | 9/1953 | O'Meara | |
| 2,801,002 A | * | 7/1957 | Volckening et al. | 206/472 |
| 2,915,173 A | | 12/1959 | Langdon | |
| 3,119,495 A | | 1/1964 | Pratt | |
| 3,341,003 A | | 9/1967 | Marsh | |
| 3,346,104 A | | 10/1967 | Marsh | |
| 3,403,776 A | | 10/1968 | Denny | |
| 3,515,265 A | | 6/1970 | Bartnik | |
| 3,680,772 A | | 8/1972 | Hoover | |
| 3,780,857 A | | 12/1973 | Rosano | |
| 3,795,309 A | | 3/1974 | Link | |
| 3,942,634 A | | 3/1976 | Gandi et al. | |
| 4,189,053 A | | 2/1980 | Stagnitto et al. | |
| 4,344,532 A | | 8/1982 | Eldridge, Jr. et al. | |
| 4,811,845 A | | 3/1989 | Baggett | |
| 5,109,984 A | | 5/1992 | Romick | |

(Continued)

OTHER PUBLICATIONS

International Search Report, Application No. PCT/US09/58683 dated Nov. 11, 2009.

*Primary Examiner* — Bryon Gehman
(74) *Attorney, Agent, or Firm* — Elias Domingo, Esq.

(57) ABSTRACT

The present disclosure relates to medical packaging for the accommodation of medical supplies. The medical packaging discussed herein has a plurality of panels, including a first panel, a second panel, and a third panel, that are releasably secured together to establish a first sterile environment between the first panel and the second panel for the retention of a first medical supply, and a second sterile environment between the second panel and the third panel for the retention of a second medical supply. The panels are configured for relative movement such that movement of the first panel relative to the second panel reveals the first medical supply without compromising the second sterile environment, and movement of the second panel relative to the third panel reveals the second medical supply. The panels are arranged for sequential separation in accordance with the steps of the procedure in which the medical supplies are employed.

18 Claims, 8 Drawing Sheets

U.S. PATENT DOCUMENTS

| | | |
|---|---|---|
| 5,203,457 A | 4/1993 | Garcia |
| 5,291,990 A | 3/1994 | Sejzer |
| 5,803,499 A | 9/1998 | Tung et al. |
| 5,894,923 A | 4/1999 | Hamstra et al. |
| 5,931,303 A | 8/1999 | Salvadori |
| 6,012,586 A | 1/2000 | Misra |
| 6,073,767 A | 6/2000 | Cohen et al. |
| 6,225,522 B1 | 5/2001 | Schroeder |
| 6,669,236 B1 | 12/2003 | Hollwarth-Oberholz |
| 6,715,609 B1 | 4/2004 | Gupton |
| 6,740,068 B1 | 5/2004 | Aruffo et al. |
| 7,126,879 B2 | 10/2006 | Snyder |
| 7,293,654 B1 | 11/2007 | Wilson, Jr. et al. |
| 7,673,754 B2 | 3/2010 | Wilson, Jr. et al. |
| 2006/0151347 A1 | 7/2006 | Grossman |
| 2007/0131577 A1 | 6/2007 | Call |
| 2008/0155941 A1 | 7/2008 | Williams-Hartman |

\* cited by examiner

FOLDABLE STERILE MEDICAL PACKAGE

CROSS-REFERENCE TO RELATED APPLICATIONS

This application is a continuation application of and claims the benefit of priority under 35 U.S.C. §120 to U.S. patent application Ser. No. 12/569,047, filed on Sep. 29, 2009, now U.S. Pat. No. 7,967,139, which claims the benefit of, and priority to, U.S. Provisional Patent Application No. 61/100,796, filed on Sep. 29, 2008, now expired, the entire contents of each application identified above being incorporated by reference herein in its entirety for all purposes.

BACKGROUND

1. Technical Field

The present disclosure relates generally to a foldable package. More specifically, the present disclosure relates to a foldable package for the accommodation of medical supplies.

2. Related Art

The packaging of medical supplies presents a particular concern given the general necessity to maintain such supplies in a sterile environment. The packaging must not only preserve the sterility of the medical supplies at all times during transport, but must also protect the medical supplies from damage that may be sustained during handling and/or storage. Any rupturing, piercing, or damage to the packaging may compromise the integrity of the sterile environment, thus resulting in the use of a potentially unsafe product, the communication of undesirable substances or agents to a patient, and perhaps even infection.

Generally, medical supply packaging will include the instruments that will be used during the course of the procedure, in addition to the corresponding instruction-for-use (I.F.U.). Either prior to, or during the medical procedure, the packaging is opened to expose the instruments, and the I.F.U. is generally removed and set aside for later reference by a practitioner. However, accessing the instruments and the I.F.U. in this way unnecessarily exposes the entire contents of the package to the ambient, and clutters the work environment by separating the medical instruments from the I.F.U. and the packaging. Accordingly, there exists a need in the art for improved packaging that will address these issues.

SUMMARY

In one aspect of the present disclosure, a medical package is disclosed that is configured and dimensioned to accommodate medical supplies employable during a medical procedure. The medical package has a plurality of panels, including a first panel, a second panel, and a third panel.

The panels are releasably secured together to establish a first sterile environment between the first panel and the second panel for retention of a first medical supply, and a second sterile environment is established between the second panel and the third panel for retention of a second medical supply. The panels are configured for relative movement such that movement of the first panel relative to the second panel reveals the first medical supply without compromising the second sterile environment, and movement of the second panel relative to the third panel reveals the second medical supply. The panels are arranged for sequential separation in accordance with a plurality of steps performed during the medical procedure that are described in corresponding instructions for use supported on the first panel.

The first panel is movable relative to the second panel in a first direction, and the second panel is movable relative to third panel in a second direction, wherein the first direction and the second direction are different. To facilitate manual manipulation of the panels, the first panel may include a first tab, the second panel may include a second tab, and the third panel may include a third tab.

The plurality of panels may be fixedly attached to one another, or alternatively, at least one of the plurality of panels may be removable from the medical package. Additionally, it is envisioned that the plurality of panels may be foldably interconnected, e.g., through a plurality of living hinges.

In an alternative embodiment, the medical package further includes a fourth panel that is releasably secured to the third panel to establish a third sterile environment therebetween for retention of a third medical supply. To reveal the third medical supply, the third panel is configured for movement relative to the fourth panel in the second direction. The fourth panel may include a fourth tab configured to facilitate manual manipulation of the fourth panel.

In another embodiment, the medical package further includes a fifth panel that is releasably secured to the fourth panel such that a fourth sterile environment is established therebetween for retention of a fourth medical supply. The fourth panel is configured for movement relative to the fifth panel in the second direction to reveal the fourth medical supply. The fifth panel may include a fifth tab configured to facilitate manual manipulation of the fifth panel. In this embodiment, the third panel is configured for movement relative to the fourth panel to reveal the third medical supply without compromising the fourth sterile environment.

In another aspect of the present disclosure, a medical package is disclosed that is configured and dimensioned to accommodate medical supplies employable during a medical procedure. The medical package has a plurality of panels including a first panel, a second panel, and a third panel. The first and second panels are releasably secured together to establish a first sterile environment therebetween for retention of a first medical supply, and the second and third panels are releasably secured together such that a second sterile environment is established therebetween for retention of a second medical supply. The first panel is movable relative to the second panel from a first position, in which the first medical supply remains concealed within the first sterile environment, to a second position, in which the first medical supply is revealed, and the second panel is movable relative to the third panel from a first position, in which the second medical supply remains concealed within the second sterile environment, to a second position, in which the second medical supply is revealed. The plurality of panels are arranged for sequential separation in accordance with a plurality of steps performed during the medical procedure.

In a final aspect of the present disclosure, a medical procedure is disclosed that includes the step of providing a medical package with a plurality of panels including at least a first panel, a second panel, and a third panel. The plurality of panels are releasably secured together to establish a first sterile environment between the first panel and the second panel for retention of a first medical supply, and a second sterile environment between the second panel and the third panel for retention of a second medical supply. The plurality of panels are configured for relative movement such that movement of the first panel relative to the second panel reveals the first medical supply without compromising the second sterile environment, and movement of the second panel relative to the third panel reveals the second medical supply.

In addition, the method includes the steps of moving the first panel relative to the second panel to reveal the first medical supply, using the first medical supply, moving the second panel relative to the third panel to reveal the second medical supply, and using the second medical supply.

These and other features of the medical packaging and procedure disclosed herein will become more readily apparent to those skilled in the art through reference to the detailed description of the various embodiments of the present disclosure below.

BRIEF DESCRIPTION OF THE DRAWINGS

The accompanying drawings, which are incorporated in, and constitute a part of this specification, illustrate various exemplary embodiments of the present disclosure. Together with the general description given above, and the detailed description of the embodiments given below, the accompanying drawings serve to explain the principles of the medical packaging and method disclosed herein.

DETAILED DESCRIPTION

Figure 1:
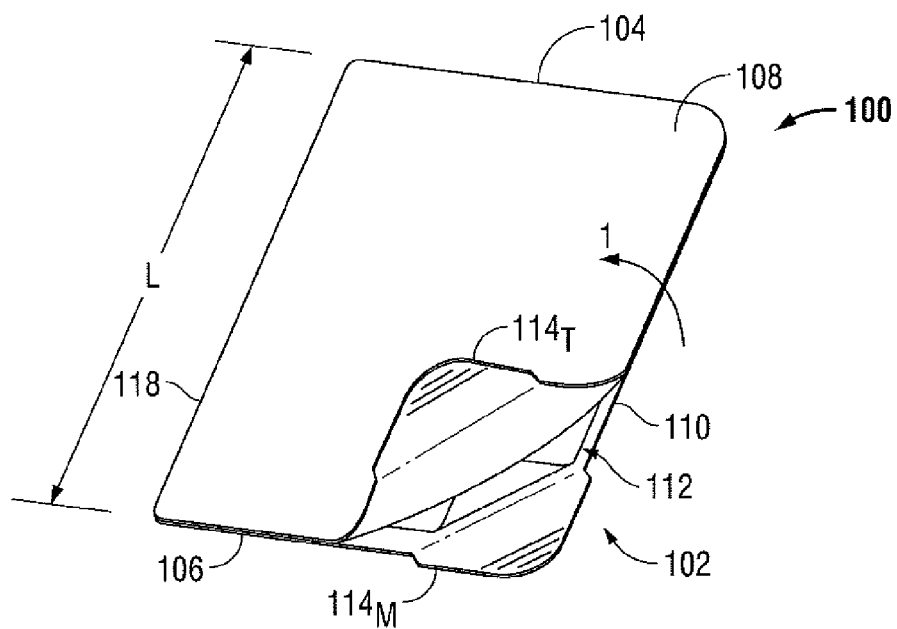
FIG. 1 is a top, perspective view of one embodiment of a medical package, in accordance with the principles of the present disclosure, that includes a top panel, a bottom, panel, and a plurality of intermediate panels positioned therebetween for the accommodation of medical supplies.

Various embodiments of the presently disclosed medical packaging and procedure will now be described in detail with reference to the foregoing figures wherein like reference characters identify similar or identical elements.

In the figures, and in the description which follows, the various embodiments of the disclosed medical packaging and procedure will be discussed in connection with an intravenous (IV) catheter protection system. However, one skilled in the art will envision that the medical packaging discussed herein below may be used in connection with any medical instruments or supplies, either presently known or later devised. Without departing from the scope and spirit of the present disclosure.

FIGS. 1-8 illustrate one embodiment of a medical package 100 that houses and accommodates the aforementioned IV catheter protection system in a sterile environment until the medical package 100 is opened by a practitioner. The IV catheter protection system includes a swab 10 (FIG. 2), a first collection of securement tape 12 (FIG. 4), a dressing 14 (FIG. 6), and a second collection of securement tape 16 (FIG. 8) in addition to a label 18. The method of use corresponding to the IV catheter protection system includes four steps that are outlined for the practitioner on instructions-for-use I.F.U. (FIGS. 2-8) that are supplied with the medical package 100.

The medical package 100 may be formed from any suitable material, including but not limited to paperboard, coated papers, polymer films, spunbound polymer fibers (e.g., TYVEK®), metalized polymer films, foils, and the like, either exclusively or in combination, and includes a plurality of panels 102 (FIG. 1) extending from a top edge 104 to a bottom edge 106 to define a length "L." In the specific embodiment illustrated in FIGS. 1-8, the medical package 100 includes a top panel 108, a bottom panel 110, and plurality of intermediate panels 112.

Figure 2:
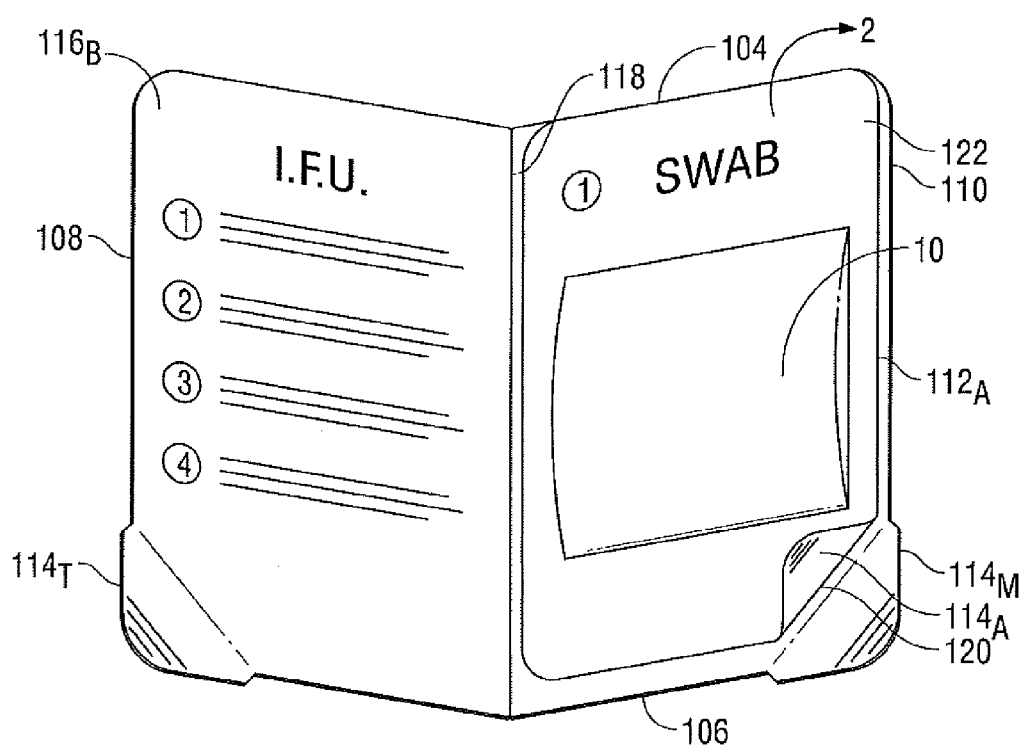
FIG. 2 is a top, perspective view of the medical package of FIG. 1 after lifting the top panel to expose a first intermediate panel, and a swab positioned thereon, for using during a surgical procedure.

As can be ascertained through reference to FIGS. 1 and 2, the top panel 108 is connected to the bottom panel 110 along the length "L" through the employ of a living hinge 118 such that the top panel 108 is movable in the direction indicated by arrow 1. However, in alternative embodiments of the medical package 100, any binding suitable for the intended purpose of facilitating opening and closing of the medical package 100 may be used. Prior to opening the medical package 100, the respective top and bottom panels 108, 110 are releasably secured along the peripheries thereof. The respective top and bottom panels 108, 110 may be secured together in any manner suitable for the intended purpose of establishing and maintaining a sterile environment therebetween until such time that a practitioner intentionally opens the medical package 100. For example, it is envisioned that the respective top and bottom panels 108, 110 may be attached through the use of a medical grade, sterile adhesive (not shown). The top and bottom panels 108, 110 include tabs $114_T$ and $114_M$, respectively, which are each configured for grasping by the practitioner to facilitate separation of the top panel 108 from the bottom panel 110, and thus opening of the medical package 100.

The top panel 108 defines a bottom face $116_B$ (FIG. 2) that accommodates the I.F.U. outlining the use of the IV catheter protection system. The I.F.U. may be either removably attached to the bottom face $116_B$ of the top panel 108, or alternatively, the I.F.U. may be fixedly or integrally formed therewith. For example, the I.F.U. may be fastened to the bottom face $116_B$ of the top panel 108, e.g., through the use of sterile adhesive, or the I.F.U. may be written or inscribed thereon. Positioning the I.F.U. on the bottom face $116_B$ of the top panel 108 allows the I.F.U. to remain visible to the practitioner at all times during the medical procedure, as will be discussed in further detail below.

Referring again to FIGS. 1-8, the aforementioned intermediate panels 112 are positioned between the top panel 108 and the bottom panel 110. The intermediate panels 112 are arranged such that they are exposed sequentially according to the order in which the steps of the corresponding medical procedure are performed, as outlined in the I.F.U. The intermediate panels 112 support a number of the medical supplies included in the medical package 100. As such, in the embodiment of the medical package 100 seen in FIGS. 1-8, the intermediate panels 112 support individual components of the intravenous (IV) catheter protection system. Specifically, the intermediate panels 112 include a first intermediate panel $112_A$ (FIG. 2) supporting the swab 10, a second intermediate panel $112_B$ (FIG. 4) supporting the first collection of securement tape 12, and a third intermediate panel $112_C$ (FIG. 6) supporting the dressing 14. In alternate embodiments of the medical package 100, however, greater or fewer numbers of intermediate panels 112 may be included depending upon the number of individual medical supplies accommodated by the medical package 100. The final component of the IV catheter protection system, i.e., the second collection of securement tape 16 and the label 18, are supported on a top face $116_T$ of the bottom panel 110, rather than on an additional intermediate panel 112, to reduce the overall number of components in the medical package 100, and thus, decrease manufacturing costs. However, an embodiment of the medical package 100 including a plurality of intermediate panels 112 corresponding in number to the number of components housed by the medical package 100, i.e., an embodiment wherein the top face $116_T$ (FIG. 3) of the bottom panel 110 does not support any medical supplies, is not beyond the scope of the present disclosure.

The first intermediate panel $112_A$ includes a tab $114_A$, the second intermediate panel $112_B$ includes a tab $114_B$, and the third intermediate panel $112_C$ includes a tab $114_C$. As discussed above with respect to the tabs $114_T$, $114_M$ respectively included on the top and bottom panels 108, 110, the tabs $114_A$, $114_B$, $114_C$ are each configured for grasping by the practitioner to facilitate separation of the respective first, second, and third intermediate panels $112_A$, $112_B$, $112_C$, and thus, exposure of the components of the IV catheter protection system retained within the medical package 100 in accordance with the procedure set forth below.

When the medical package 100 is assembled, a bottom face $116_B$ (FIG. 3) of the first intermediate panel $112_A$ is releasably secured to a top face $116_T$ of the second intermediate panel $112_B$, a bottom face $116_B$ (FIG. 5) of the second intermediate panel $112_B$ is releasably secured to a top face $116_T$ of the third intermediate panel $112_C$, and a bottom face $116_C$ (FIG. 7) of the third intermediate panel $112_C$ is releasably secured to the top face $116_T$ of the bottom panel 110. It is also envisioned that intermediate panel $112_A$ may be larger in size than intermediate panel $112_B$ and that intermediate panel intermediate panel $112_B$ may be larger in size than intermediate panel $112_C$ such that intermediate panels $112_A$, $112_B$, $112_C$ are each releasably secured to the top face $116_T$ of the bottom panel 110. As discussed above with respect to the top panel 108 and the bottom panel 110, the respective first, second, and third intermediate panels $112_A$, $112_B$, $112_C$, and the bottom panel 110, may be attached in any manner suitable for the intended purpose of establishing and maintaining a sterile environment therebetween, e.g., through the use of a medical grade, sterile adhesive (not shown). In the embodiment of the medical package 100 seen in FIGS. 1-8, the intermediate panels $112_A$, $112_B$, $112_C$ are connected to each other, and/or to the bottom panel 110, at one or more points along the top edge 104 such that the intermediate panels $112_A$, $112_B$, $112_C$ can be moved in the direction indicated by arrow 2. To facilitate movement of the intermediate panels $112_A$, $112_B$, $112_C$ in the direction of arrow 2, the tabs $114_A$, $114_B$, $114_C$ may be positioned in the lower right-hand corners 120 of the respective first, second, and third intermediate panels $112_A$, $112_B$, $112_C$, as seen in FIGS. 2-8, or in any other suitable location.

Figure 3:
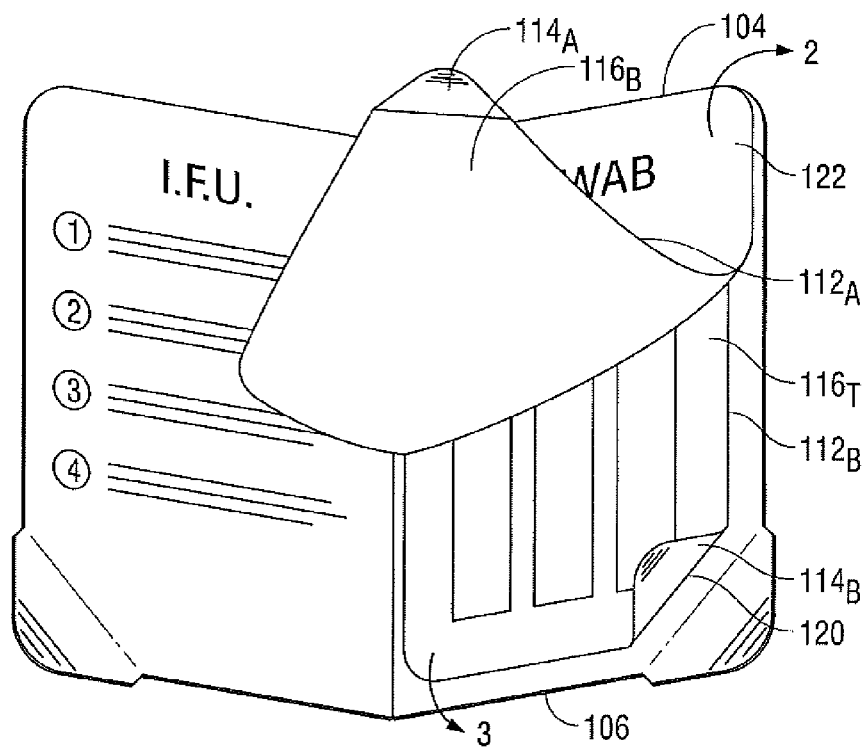
FIG. 3 is a top, perspective view of the medical package seen in FIG. 1 illustrating movement of the first intermediate panel to expose a second intermediate panel.

In an alternative embodiment of the medical package 100, it is envisioned that the intermediate panels $112_A$, $112_B$, $112_C$ may be connected to each other, and/or the bottom panel 110, at one or more points along the bottom edge 106 such that the intermediate panels $112_A$, $112_B$, $112_C$ can be moved in the direction of arrow 3 (FIG. 3). In this embodiment, the tabs $114_A$, $114_B$, $114_C$ may be respectively positioned on the first, second, and third intermediate panels $112_A$, $112_B$, $112_C$ in any suitable location, such as an upper right-hand corner 122 of the intermediate panels $112_A$, $112_B$, $112_C$.

The connections between the intermediate panels $112_A$, $112_B$, $112_C$, and the bottom panel 110, may be fixed, such that the intermediate panels $112_A$, $112_B$, $112_C$ are simply folded in the direction of arrow 2, and thus remain integrally formed components of the medical package 100. Alternatively, however, the connections between the intermediate panels $112_A$, $112_B$, $112_C$, and the bottom panel 110, may detachable, such that the intermediate panels $112_A$, $112_B$, $112_C$ are removable from the medical package 100 after separation from an adjacent panel 102 and/or the bottom panel 110.

Referring still to FIGS. 1-8, use of the medical package 100 will be discussed. To open the medical package 100, the practitioner grasps the tab $114_T$ (FIG. 1) included on the top panel 108, and lifts the top panel 108 in the direction indicated by arrow 1 to thereby separate the top panel 108 from the bottom panel 110, and expose the swab 10 (FIG. 2). Following separation of the top panel 108 from the bottom panel 110, it should be appreciated that the integrity of the sterile environment established between the intermediate panels 112 and the bottom panel 110 remains intact, and that the becomes exposed for reference by the practitioner. After opening the medical package 100, the practitioner can utilize the swab 10 to clean the site where the IV catheter (not shown) will be inserted.

Figure 4:
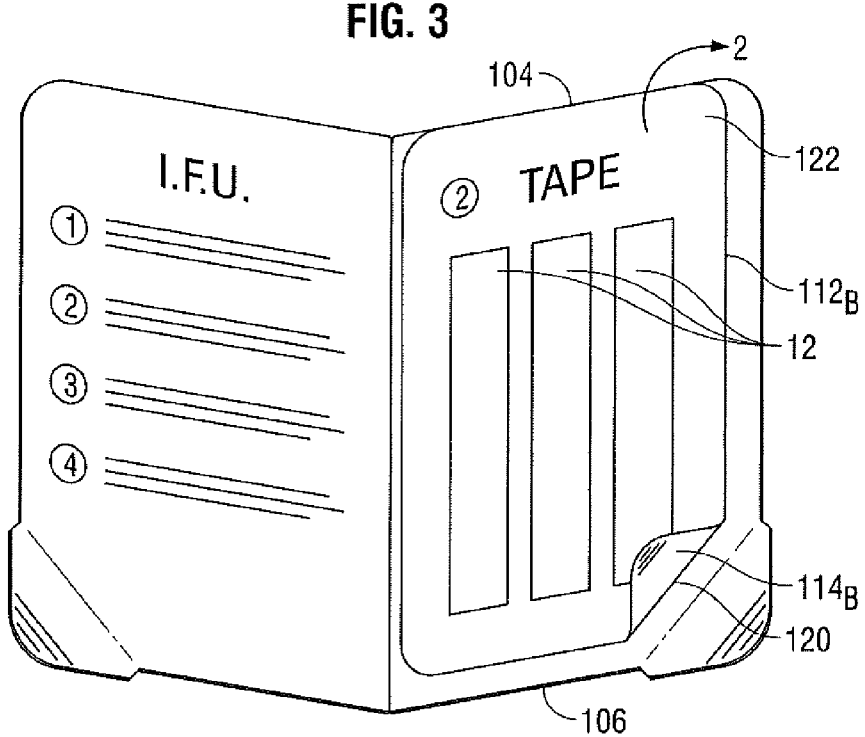
FIG. 4 is a top, perspective view of the medical package seen in FIG. 3 illustrating the second intermediate panel, and a first collection of securement tape positioned thereon, for using during the surgical procedure.

Following use of the swab 10 and insertion of the IV catheter (not shown), as seen in FIGS. 2 and 3, the practitioner can grasp the tab $114_A$ included on the first intermediate panel $112_A$, and lift the first intermediate panel $112_A$ in the direction indicated by arrow 2 to thereby separate the first intermediate panel $112_A$ from the second intermediate panel $112_B$, and expose the first collection of securement tape 12 (FIG. 4).

Following separation of the first intermediate panel $112_A$ from the second intermediate panel $112_B$, the sterile environment previously established between the intermediate panels $112_B$, $112_C$ and the bottom panel 110 remains uncompromised.

By positioning the I.F.U. on the bottom face $116_B$ (FIG. 2) of the top panel 108, and moving the first intermediate panel $112_A$ in the direction of arrow 2, the practitioner remains in plain view of the I.F.U. such that the practitioner can continually reference the I.F.U. and prepare for the next step in the medical procedure. Thereafter, the practitioner can utilize the first collection of securement tape 12 to limit relative movement between the IV catheter (not shown) and the patient's skin.

Figure 5:
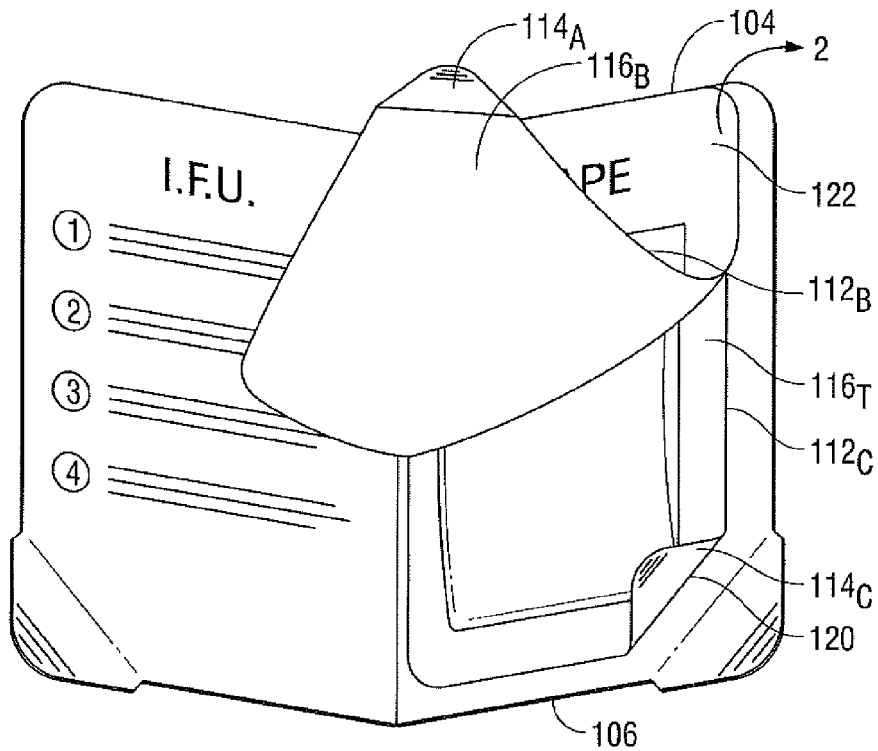
FIG. 5 is a top, perspective view of the medical package seen in FIG. 4 illustrating movement of the second intermediate panel to expose a third intermediate panel.
Figure 6:
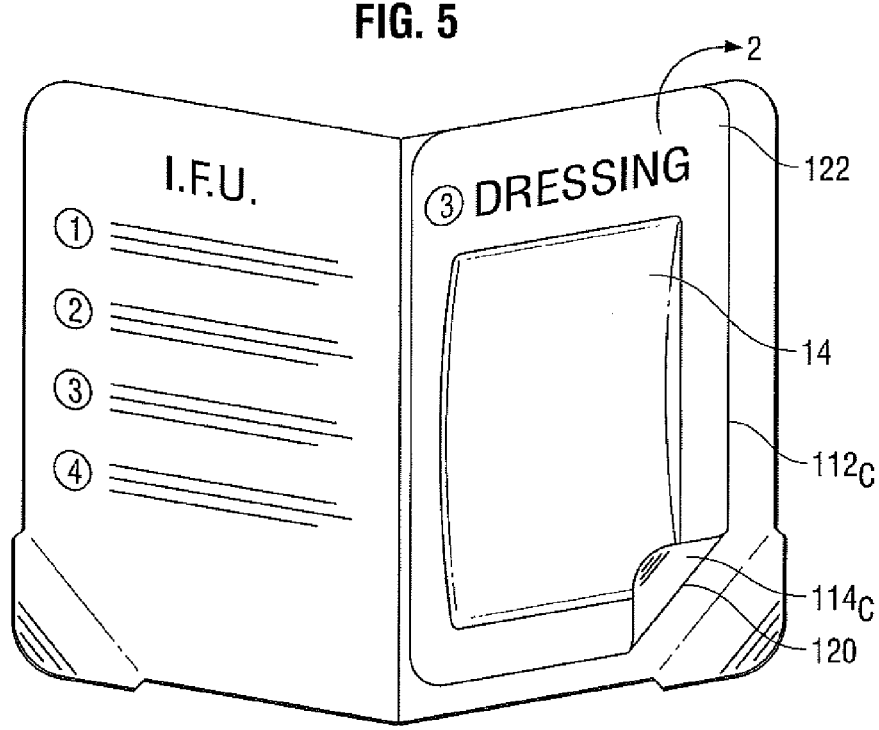
FIG. 6 is a top, perspective view of the medical package seen in FIG. 5 illustrating the third intermediate panel, and a dressing positioned thereon, for using during the surgical procedure.

With reference to FIGS. 4 and 5, the practitioner can then grasp the tab $114_B$ included on the second intermediate panel $112_B$, and lift the second intermediate panel $112_B$ in the direction indicated by arrow 2 to thereby separate the second intermediate panel $112_B$ from the third intermediate panel $112_C$, and expose the dressing 14 (FIG. 6). Following separation of the second intermediate panel $112_B$ from the third intermediate panel $112_C$, the sterile environment previously established between the third intermediate panel $112_C$ and the bottom panel 110 remains uncompromised, and the remains visible for reference by the practitioner. Thereafter, the practitioner can position the dressing 14 as desired.

Figure 7:
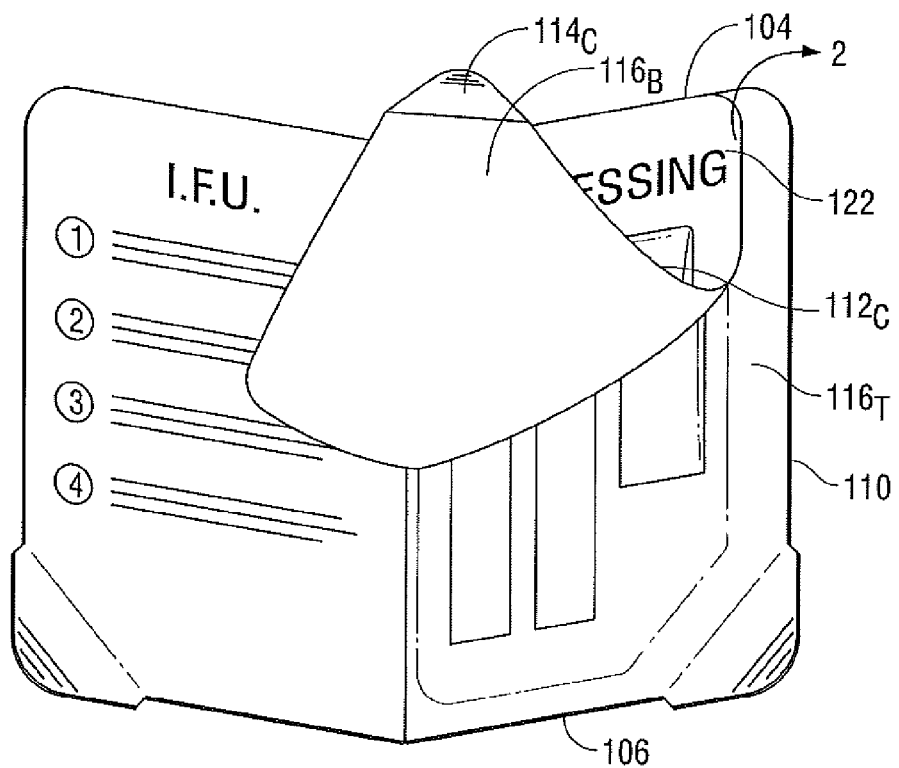
FIG. 7 is a top, perspective view of the medical package seen in FIG. 6 illustrating movement of the third intermediate panel to expose the bottom panel.
Figure 8:
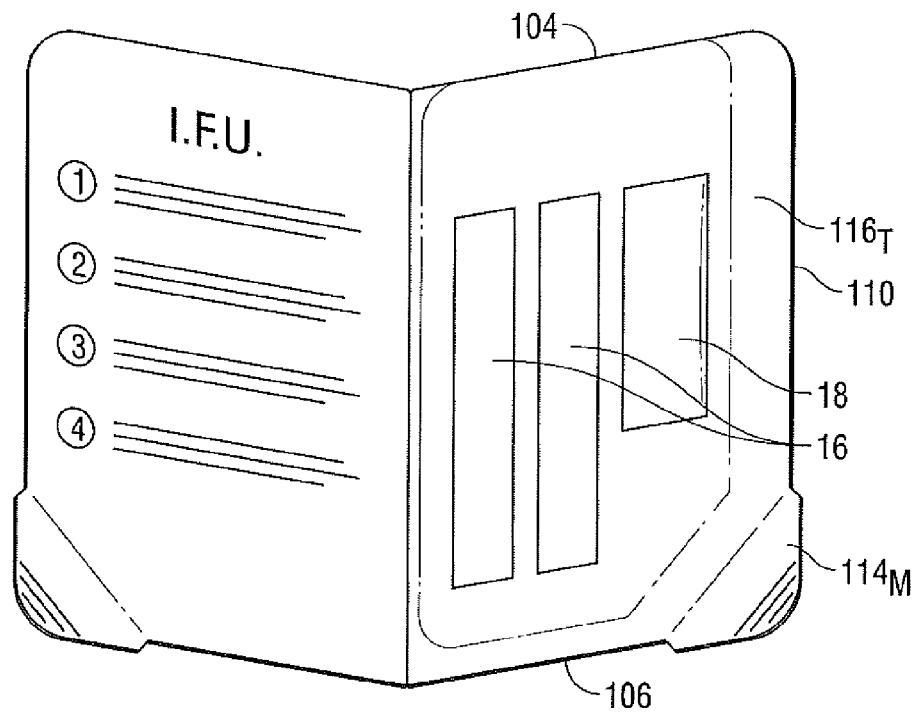
FIG. 8 is a top, perspective view of the medical package seen in FIG. 7 illustrating the bottom panel, and a second collection of securement tape, together with a label, positioned thereon, for using during the surgical procedure.
Figure 9:
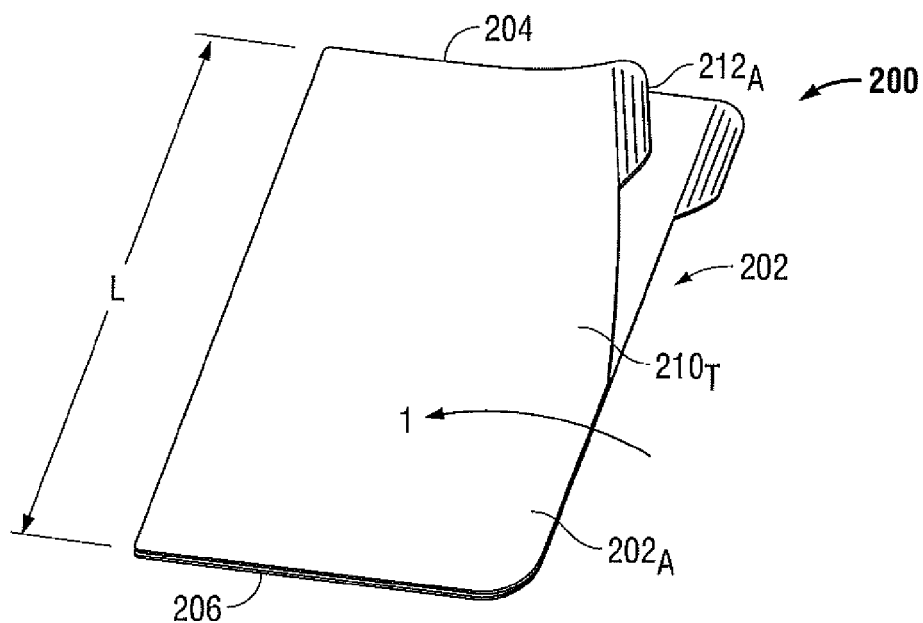
FIG. 9 is a top, perspective view of another embodiment of a medical package, in accordance with the principles of the present disclosure, that includes a plurality of panels for the accommodation of medical supplies.

Finally, referring to FIGS. 7 and 8, the practitioner can grasp the tab $114_C$ included on the third intermediate panel $112_C$, and lift the third intermediate panel $112_C$ in the direction indicated by arrow 2 to thereby separate the third intermediate panel $112_C$ from the bottom panel 110, and expose the second collection of securement tape 16 and the label 18 (FIG. 8). The practitioner can then use the second collection of securement tape 16 to further limit relative movement between the IV catheter (not shown) and the patient's skin, as well as the label 18.

With reference now to FIGS. 9-16, an alternative embodiment of the medical package, referred to generally by the reference character 200, will be discussed. The medical package 200 is substantially similar to the medical package 100 discussed above with respect to FIGS. 1-8, and accordingly, will only be discussed with respect to its differences therefrom.

Figure 13:
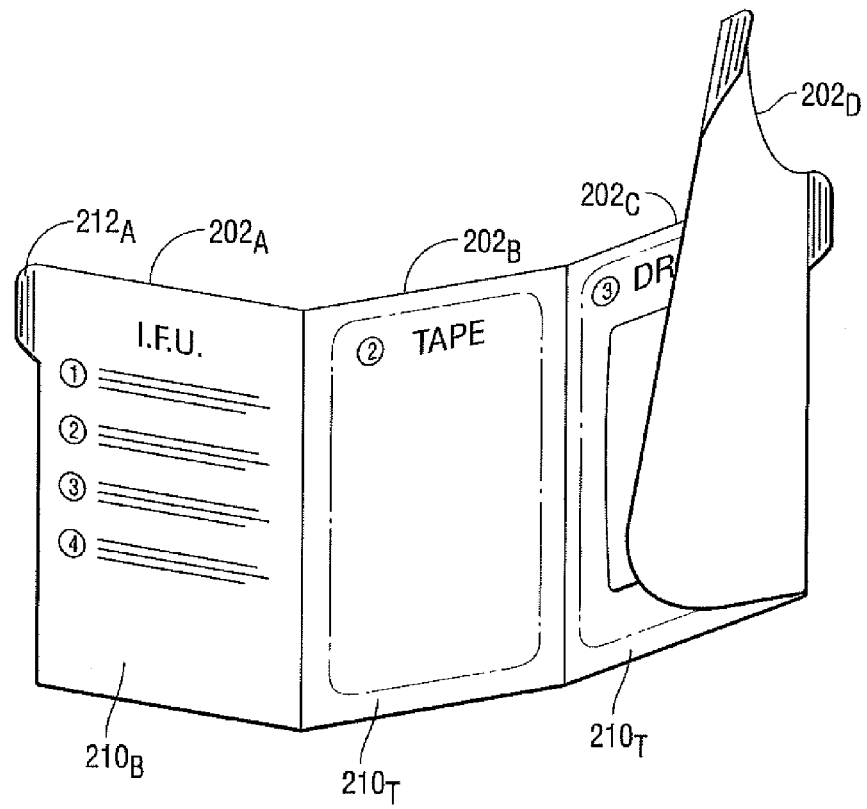
FIG. 13 is a top, perspective view of the medical package seen in FIG. 12 illustrating movement of the fourth panel to expose a top face of the third panel and a backing panel positioned on a top face of the fourth panel.
Figure 14:
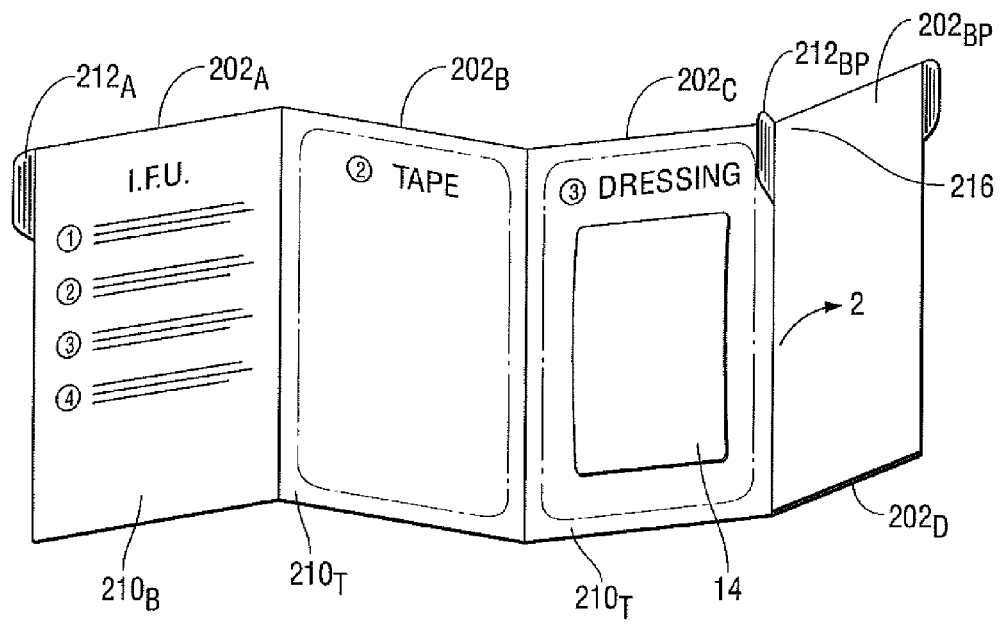
FIG. 14 is a top, perspective view of the medical package seen in FIG. 13 illustrating the top face of the third panel, a dressing positioned on the top face of the third panel for use during the surgical procedure, and the backing panel.
Figure 15:
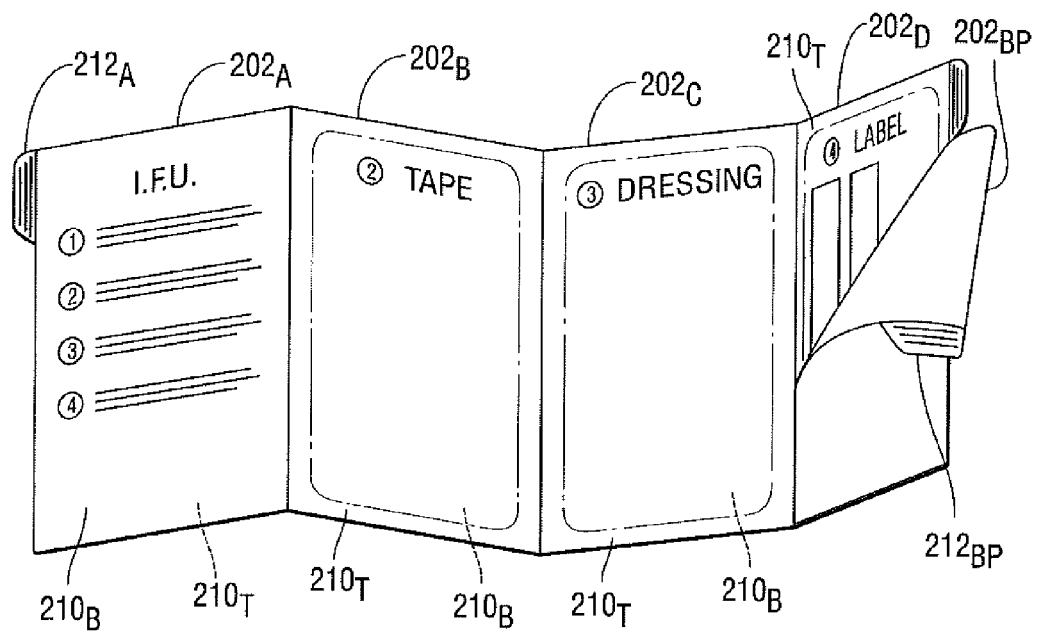
FIG. 15 is a top, perspective view of the medical package seen in FIG. 14 illustrating movement of the backing panel to expose the top face of the fourth panel.

The medical package 200 includes a plurality of panels 202 extending from a top edge 204 to a bottom edge 206 to define a length "L," as well as a backing panel $202_{BP}$ (FIGS. 14 and 15). In the embodiment of the medical package seen in FIGS. 9-16, the medical package 200 houses the components of the IV catheter protection system discussed above, and is thus illustrated as including a first panel $202_A$, a second panel $202_B$, a third panel $202_C$, and a fourth panel $202_D$, in addition to the aforementioned backing panel $202_{BP}$. However, alternate embodiments of the medical package 200 are also envisioned that may include greater or fewer numbers of panels 202 dependent upon the medical supplies intended to be accommodated thereby.

Figure 16:
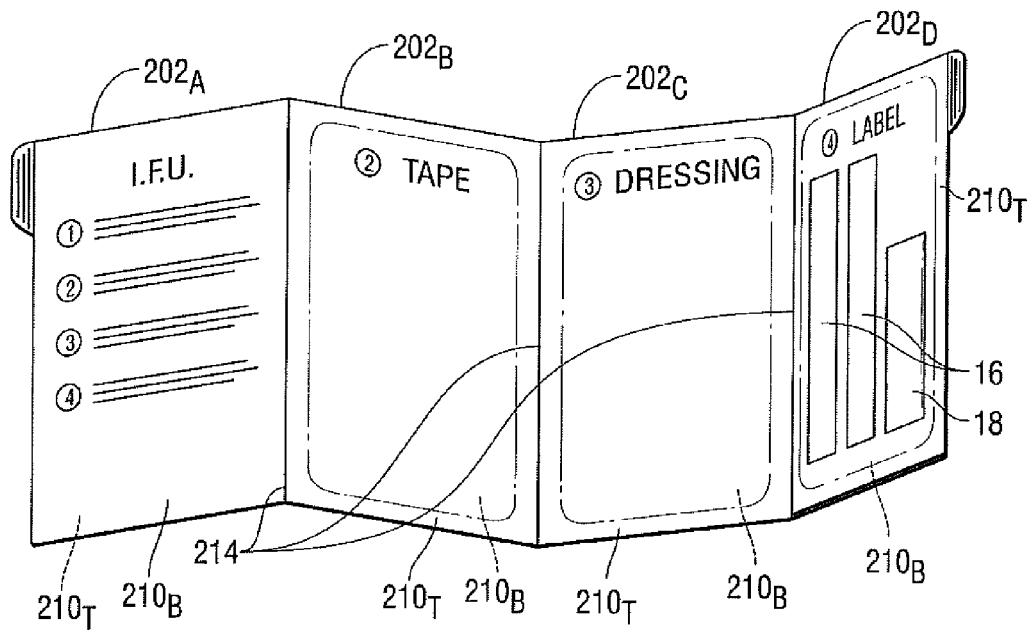
FIG. 16 is a top, perspective view of the medical package seen in FIG. 15 illustrating the top face of the fourth panel, and a second collection of securement tape, together with a label, positioned thereon, for use during the surgical procedure.

The first panel $202_A$ includes a bottom face $210_B$, a top face $210_T$, and a tab $212_A$, the second panel $202_B$ includes an bottom face $210_B$ and a top face $210_T$, the third panel $202_C$ includes a bottom face $210_B$ having a tab $212_C$ affixed thereto and a top face $210_T$, and the fourth panel $202_D$ includes a bottom face $210_B$ having a tab $212_D$ affixed thereto and a top face $210_T$. As seen in FIGS. 14 and 15, the fourth panel $202_D$ also includes the aforementioned backing panel $202_{BP}$. The backing panel $202_{BP}$ has a tab $212_{BP}$ affixed thereto, and is releasably attached to the top face $210_T$ of the fourth panel $202_D$ such that a sterile environment is established therebetween, e.g., through the use of a medical grade, sterile adhesive (not shown). The plurality of panels 202 are connected along their length "L" (FIG. 1) through the employ of a plurality of living hinges 214, which are best seen in FIG. 16. However, any binding suitable for the intended purpose of facilitating opening and closing of the medical package 200 may be used.

Figure 10:
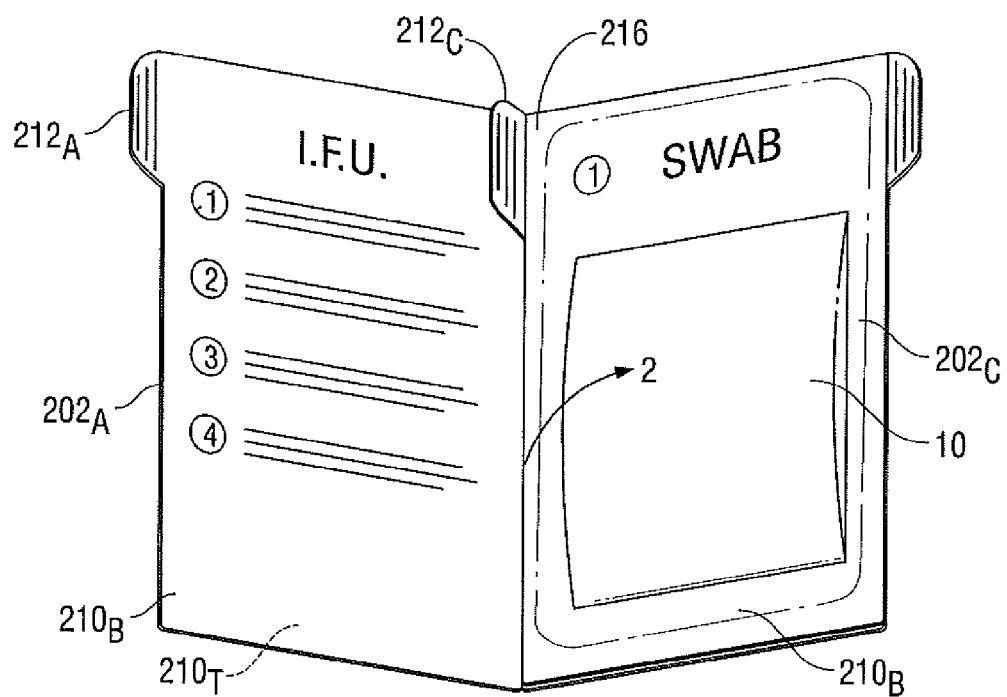
FIG. 10 is a top, perspective view of the medical package seen in FIG. 9 after lifting a first panel and illustrating a bottom face of a third panel, and a swab positioned thereon, for use during a surgical procedure.

The bottom face $210_B$ of the first panel $202_A$ accommodates the I.F.U. pertaining to use of the IV catheter protection system, which may be either releasably connected to the bottom face $210_B$, or integrally formed therewith, as discussed above with respect to, the medical package 100 illustrated in FIGS. 1-8. The top face $210_T$ of the second panel $202_B$ accommodates the first collection of securement tape 12 (FIG. 12), the top face $210_T$ of the third panel $202_C$ accommodates the dressing 14 (FIG. 14), the top face $210_T$ of the fourth panel $202_D$ accommodates the second collection of securement tape 16 and the label 18 (FIG. 16), which are positioned beneath the backing panel $202_{BP}$ secured to the fourth panel $202_D$, and the bottom face $210_B$ of the third panel $202_C$ accommodates the swab 10 (FIG. 10).

As discussed above with respect to the medical package 100 seen in FIGS. 1-8, the medical package 200 is assembled such that the practitioner will sequentially expose the components of the IV catheter protection system according to the order in which the steps of the corresponding medical procedure are performed, as outlined in the I.F.U. Specifically, in the embodiment of the medical package seen in FIGS. 9-16, the medical package 200 is assembled such that the bottom face $210_B$ of the first panel $202_A$ is releasably attached to the bottom face $210_B$ of the third panel $202_C$, the top face $210_T$ of the second panel 202 is releasably attached to the bottom face $210_B$ of the fourth panel $202_D$, and the top face $210_T$ of the third panel 202 is releasably attached to the top face $210_T$ of the fourth panel $202_D$. However, additional arrangements for the medical package 200 are not beyond the scope of the present disclosure.

The panels 202 may be attached in any manner suitable for the intended purpose of establishing and maintaining a sterile environment between adjacent panels 202 (FIG. 1), e.g., through the use of a medical grade, sterile adhesive (not shown), until such time that the practitioner intentionally separates adjacent panels 202 to open the medical package 200.

With continued reference to FIGS. 9-16, use of the medical package 200 will be discussed. To open the medical package 200, the practitioner grasps the tab $212_A$ included on the first panel $202_A$, and lifts the first panel $202_A$ in the direction indicated by arrow 1 (FIG. 9) to separate the bottom face $210_B$ of the first panel $202_A$ from the bottom face $210_B$ of the third panel $202_C$, and thereby expose the swab 10 (FIG. 2) and the I.F.U. for reference by the practitioner during the medical procedure. Thereafter, the practitioner can utilize the swab 10 to clean the site where the IV catheter (not shown) will be inserted.

Figure 11:
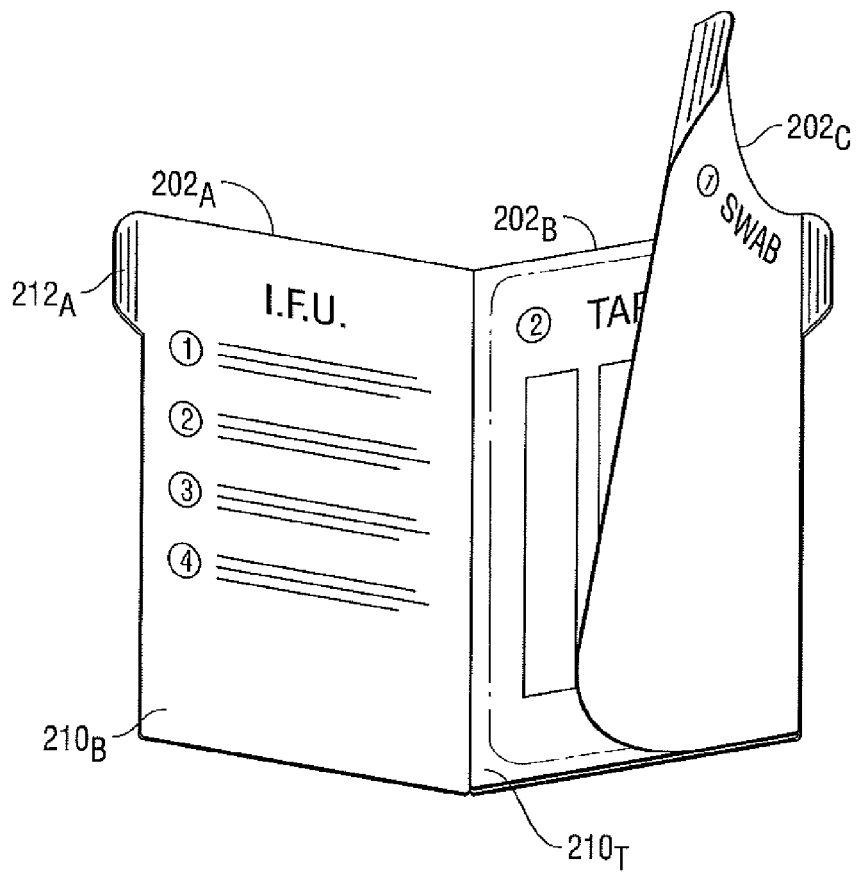
FIG. 11 is a top, perspective view of the medical package seen in FIG. 10 illustrating movement of the third panel to expose a top face of a second panel.
Figure 12:
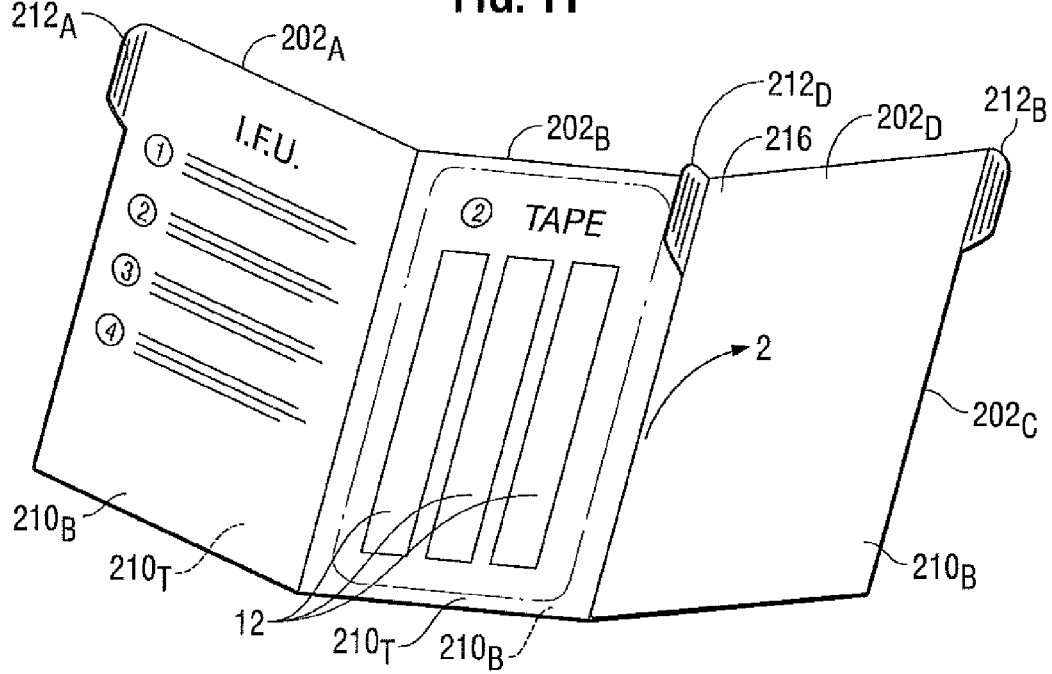
FIG. 12 is a top, perspective view of the medical package seen in FIG. 11 illustrating the top face of the second panel, a first collection of securement tape positioned on the top face of the second panel for use during the surgical procedure, and a bottom face of a fourth panel.

With specific reference to FIGS. 10 and 11, following use of the swab 10 and insertion of the IV catheter (not shown), the practitioner can grasp the tab $212_C$ included on the bottom face $210_B$ of the third panel $202_C$, and use the tab $212_C$ to move the third panel $202_C$ in the direction indicated by arrow 2. Referring now to FIG. 12 as well, movement of the third panel $202_C$ in the direction of arrow 2 separates the bottom face $210_B$ of the fourth panel $202_D$ from the top face $210_T$ of the second panel $202_B$, and exposes the first collection of securement tape 12 without obscuring the practitioner's view of the I.F.U., thereby allowing the practitioner to continually reference the I.F.U., if necessary. The practitioner can then utilize the first collection of securement tape 12 to limit relative movement between the IV catheter (not shown) and the patient's skin.

After placement of the first collection of securement tape 12, with reference now to FIGS. 12-14, the practitioner can grasp the tab 212$_D$ included on the bottom face 210$_B$ of the fourth panel 202$_D$, and use the tab 212$_D$ to move the fourth panel 202$_D$ in the direction indicated by arrow 2. Movement of the fourth panel 202$_D$ in the direction of arrow 2 separates the top face 210$_T$ of the third panel 202$_C$ from the top face 210$_T$ of the fourth panel 202$_D$, and exposes the dressing 14 without obscuring the practitioner's view of the I.F.U. When the third panel 202$_C$ is separated from the fourth panel 202$_D$, the backing panel 202$_{BP}$ maintains the sterile environment previously established for the second collection of securement tape 16 and the label 18. The practitioner can then position the dressing 14 as desired.

Finally, and with reference to FIGS. 15 and 16, the practitioner can grasp and use the tab 212$_{BP}$ (FIG. 14) included on the backing panel 202$_{BP}$ to move the separate the backing panel 202$_{BP}$ from the top face 210$_T$ of the fourth panel 202$_D$ to thereby expose the second collection of securement tape 16 and the label 18. The backing panel 202$_{BP}$ can be either removably connected to the top face 210$_T$ of the fourth panel 202$_D$ as shown in FIG. 15 such that the backing panel 202$_{BP}$ can be completely removed from the medical package 200, or alternatively, the backing panel 202$_{BP}$ can be fixedly secured to the top face 210$_T$ of the fourth panel 202$_D$ at one or more locations such that the backing panel 202$_{BP}$ remains attached to the medical package 200. Following separation of the backing panel 202$_{BP}$ from the top face 210$_T$ of the fourth panel 202$_D$, the practitioner can use the second collection of securement tape 16 to further limit relative movement between the IV catheter (not shown) and the patient's skin, for example, as well as the label 18.

As illustrated in FIGS. 10-16, the tabs 212$_C$, 212$_D$ are respectively attached to the bottom face 210$_B$ of the third and fourth panels 202$_C$, 202$_D$ at the upper left-hand corner 216 thereof, and the tab 212$_{BP}$ is attached to the upper left-hand corner 216 of the backing layer 202$_{BP}$ such that the panels 202$_C$, 202$_D$ are movable in the direction of arrow 2. It should be appreciated, however, that the tabs 212$_C$, 212$_D$, 212$_{BP}$ can be alternately positioned in any location suitable for the intended purpose of facilitating movement of the third panel 202$_C$, the fourth panel 202$_D$, and the backing panel 202$_{BP}$ to expose the components of the IV catheter protection system as discussed above.

While the above is a complete description of the various embodiments of the medical package and method disclosed herein, various alternatives, modifications, and equivalents are also envisioned that do not depart from the scope or spirit of the present disclosure. For example, the features illustrated or described in connection with one exemplary embodiment may be combined with the features of other embodiments. Those skilled in the art will understand that the embodiments discussed above are intended to be non-limiting and exemplary only, and accordingly, that the present disclosure is not to be limited by what has been particularly shown and described, except as indicated by the appended claims.

The invention claimed is:

1. A medical package configured and dimensioned to accommodate medical supplies employable during a medical procedure, the medical package comprising:
a plurality of panels including a top panel, a bottom panel, and at least one intermediate panel positioned between the top panel and the bottom panel, each of the plurality of panels including longitudinal edges, and transverse edges extending in substantially orthogonal relation to the longitudinal edges, the plurality of panels being releasably secured together such that a first sterile environment is established between the top panel and the bottom panel for retention of a first medical supply and a second sterile environment is established between the bottom panel and the at least one intermediate panel for retention of a second medical supply, the plurality of panels being configured for relative movement such that movement of the top panel relative to the bottom panel reveals the first medical supply without compromising the second sterile environment, and movement of the bottom panel relative to the at least one intermediate panel reveals the second medical supply, the top panel and the bottom panel each being movable about an axis extending along one of the longitudinal edges thereof, the at least one intermediate panel being movable about an axis extending along one of the transverse edges thereof.

2. The medical package of claim 1, wherein the panels are arranged for sequential separation in accordance with a plurality of steps performed during the medical procedure and described in instructions for use.

3. The medical package of claim 2, wherein the top panel is configured and dimensioned to support the instructions for use.

4. The medical package of claim 1, wherein the top panel includes a first tab, the bottom panel includes a second tab, and the at least one intermediate panel includes a third tab, the first tab being configured to facilitate manual manipulation of the top panel, the second tab being configured to facilitate manual manipulation of the bottom panel, and the third tab being configured to facilitate manual manipulation of the at least one intermediate panel.

5. The medical package of claim 4, wherein the at least one intermediate panel includes first and second intermediate panels each including each including longitudinal edges and transverse edges extending in substantially orthogonal relation to the longitudinal edges, the first and second intermediate panels being releasably secured together such that a third sterile environment is established therebetween for retention of a third medical supply.

6. The medical package of claim 5, wherein the first and second intermediate panels are configured for relative movement about axes extending along one of the transverse edges thereof.

7. The medical package of claim 5, wherein the first intermediate panel includes the third tab, and the second intermediate panel includes a fourth tab configured to facilitate manual manipulation of the second intermediate panel.

8. The medical package of claim 5, further including a third intermediate panel releasably secured to the second intermediate panel such that a fourth sterile environment is established therebetween for retention of a fourth medical supply, the third intermediate panel including longitudinal edges, and transverse edges extending in substantially orthogonal relation to the longitudinal edges.

9. The medical package of claim 8, wherein the second and third intermediate panels are configured for relative movement about axes extending along of the transverse edges thereof to reveal the fourth medical supply.

10. The medical package of claim 8, wherein the third intermediate panel includes a fifth tab configured to facilitate manual manipulation of the third intermediate panel.

11. The medical package of claim 1, wherein the panels are fixedly attached to one another.

12. The medical package of claim 1, wherein at least one of the plurality of panels is removable from the medical package.

13. The medical package of claim 1, wherein the panels are foldably interconnected.

14. A medical package configured and dimensioned to accommodate medical supplies employable during a medical procedure, the medical package comprising:

a plurality of panels including a top panel, a bottom panel, and at least one intermediate panel positioned between the top panel and the bottom panel, each of the plurality of panels including longitudinal edges and transverse edges extending in substantially orthogonal relation to the longitudinal edges, the panels being releasably secured together to facilitate relative movement between the panels to expose at least one sterile environment retaining a medical supply, the top panel and the bottom panel each being movable about an axis extending along one of the longitudinal edges thereof, the at least one intermediate panel being movable about an axis extending along one of the transverse edges thereof, wherein a first sterile environment is established between the top panel and the bottom panel for retention of a first medical supply, and a second sterile environment is established between the bottom panel and the at least one intermediate panel for retention of a second medical supply.

15. The medical package of claim 14, wherein the panels are arranged for sequential separation in accordance with a plurality of steps performed during the medical procedure and described in instructions for use.

16. The medical package of claim 14, wherein the panels are configured for relative movement such that movement of the top panel relative to the bottom panel reveals the first medical supply without compromising the second sterile environment, and movement of the bottom panel relative to the at least one intermediate panel reveals the second medical supply.

17. The medical package of claim 14, wherein the at least one intermediate panel includes first and second intermediate panels each including longitudinal edges and transverse edges extending in substantially orthogonal relation to the longitudinal edges, the first and second intermediate panels being releasably secured together such that a third sterile environment is established therebetween for retention of a third medical supply.

18. The medical package of claim 17, wherein the first and second intermediate panels are configured for relative movement about axes extending along one of the transverse edges thereof to reveal the third medical supply.

* * * * *